(12) United States Patent
Mori et al.

(10) Patent No.: US 11,147,461 B2
(45) Date of Patent: Oct. 19, 2021

(54) BLOOD PRESSURE ANALYZING APPARATUS, BLOOD PRESSURE MEASURING APPARATUS, AND BLOOD PRESSURE ANALYZING METHOD

(71) Applicant: OMRON HEALTHCARE Co., Ltd., Kyoto (JP)

(72) Inventors: Kentaro Mori, Kyoto (JP); Shingo Yamashita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 281 days.

(21) Appl. No.: 15/919,359

(22) Filed: Mar. 13, 2018

(65) Prior Publication Data
US 2018/0199832 A1    Jul. 19, 2018

Related U.S. Application Data (63) Continuation of application No. PCT/JP2016/075436, filed on Aug. 31, 2016.

(30) Foreign Application Priority Data

Sep. 18, 2015  (JP) .............................. JP2015-185316

(51) Int. Cl.
*A61B 5/021*     (2006.01)
*A61B 5/00*      (2006.01)
(Continued)

(52) U.S. Cl.
CPC ........ *A61B 5/02108* (2013.01); *A61B 5/0205* (2013.01); *A61B 5/0225* (2013.01);
(Continued)

(58) Field of Classification Search
CPC .................................. A61B 5/02108–02125
See application file for complete search history.

(56) References Cited

U.S. PATENT DOCUMENTS 5,005,581 A    4/1991   Honeyager
5,033,471 A    7/1991   Yokoe et al.
(Continued)

FOREIGN PATENT DOCUMENTS

CN    1551742 A      12/2004
JP    S62-157504 U   10/1987
(Continued)

OTHER PUBLICATIONS

Extended European Search Report issued in European Application No. 16846255.4, dated Mar. 8, 2019 (8 pages).
(Continued)

*Primary Examiner* — Meredith Weare
(74) *Attorney, Agent, or Firm* — Osha Bergman Watanabe & Burton LLP (57) ABSTRACT

A blood pressure analyzing apparatus includes: a blood pressure variation determiner determining whether first blood pressure information varies a threshold or more from second blood pressure information or not, the first blood pressure information corresponding to an arbitrary beat, the second blood pressure information corresponding to a previous beat to the arbitrary beat; a blood pressure variation cause determiner determining whether a blood pressure variation is caused by the move of the wrist or by another reason than the move of the wrist, based on, wrist move information detected in a detection period of a pulse wave serving as a calculation source of the first blood pressure information, when it is determined that the first blood pressure information varies the threshold or more from the second blood pressure information; and a recording controller recording a determination result and the first blood pressure information in association with each other.

5 Claims, 4 Drawing Sheets

(51) Int. Cl.
*A61B 5/024* (2006.01)
*A61B 5/0205* (2006.01)
*A61B 5/0225* (2006.01)
*A61B 5/11* (2006.01)

(52) U.S. Cl.
CPC .......... *A61B 5/02416* (2013.01); *A61B 5/684* (2013.01); *A61B 5/6824* (2013.01); *A61B 5/7207* (2013.01); *A61B 5/11* (2013.01); *A61B 5/7221* (2013.01)

(56) References Cited

U.S. PATENT DOCUMENTS

| | | | |
|---|---|---|---|
| 5,439,002 | A | 8/1995 | Narimatsu et al. |
| 6,923,769 | B2 | 8/2005 | Nishii et al. |
| 9,408,542 | B1* | 8/2016 | Kinast ................ A61B 5/02125 |
| 2002/0183627 | A1 | 12/2002 | Nishii et al. |
| 2003/0109791 | A1 | 6/2003 | Kondo et al. |
| 2004/0019284 | A1 | 1/2004 | Kawaguchi et al. |
| 2005/0038327 | A1 | 2/2005 | Tanaka et al. |
| 2005/0197585 | A1* | 9/2005 | Brockway ............ A61B 5/0215 600/486 |
| 2007/0055163 | A1 | 3/2007 | Asada et al. |
| 2008/0039731 | A1* | 2/2008 | McCombie ........ A61B 5/02255 600/485 |
| 2009/0156946 | A1* | 6/2009 | Lane ...................... A61B 5/022 600/490 |
| 2011/0118613 | A1* | 5/2011 | Yokoyama ............. A61B 5/022 600/486 |
| 2011/0144456 | A1* | 6/2011 | Muhlsteff .......... A61B 5/02125 600/301 |
| 2012/0143012 | A1* | 6/2012 | Watson ............. A61B 5/02125 600/300 |
| 2015/0164437 | A1 | 6/2015 | McCombie et al. |
| 2015/0327784 | A1* | 11/2015 | Lading ................ A61B 5/0082 600/485 |
| 2015/0327785 | A1* | 11/2015 | Lading .................... A61B 8/04 600/438 |
| 2015/0327786 | A1* | 11/2015 | Lading ................ A61B 5/1126 600/437 |
| 2016/0338602 | A1* | 11/2016 | Oksala ............... A61B 5/02125 |
| 2017/0281024 | A1* | 10/2017 | Narasimhan ......... A61B 5/6824 |
| 2017/0360306 | A1* | 12/2017 | Narasimhan ......... A61B 5/0053 |

FOREIGN PATENT DOCUMENTS

| | | |
|---|---|---|
| JP | H01-242031 A | 9/1989 |
| JP | H02-001224 A | 1/1990 |
| JP | H02-261421 A | 10/1990 |
| JP | H04-161143 A | 6/1992 |
| JP | H07-124130 A | 5/1995 |
| JP | 2000-116609 A | 4/2000 |
| JP | 2000-300527 A | 10/2000 |
| JP | 2003-047601 A | 2/2003 |
| JP | 2003-199719 A | 7/2003 |
| JP | 3468705 B2 | 11/2003 |
| JP | 2004-57362 A | 2/2004 |
| JP | 2004-113368 A | 4/2004 |
| JP | 2004-223108 A | 8/2004 |

OTHER PUBLICATIONS

International Search Report issued in Application No. PCT/JP2016/075436, dated Nov. 22, 2016 (6 pages).
Written Opinion issued in Application No. PCT/JP2016/075436, dated Nov. 22, 2016 (4 pages).
International Preliminary Report on Patentability issued in Application No. PCT/JP2016/075436, dated Jul. 24, 2017 (3 pages).
Office Action issued in corresponding Chinese Application No. 201680052984.5, dated Mar. 13, 2020 (14 pages).

* cited by examiner

BLOOD PRESSURE ANALYZING APPARATUS, BLOOD PRESSURE MEASURING APPARATUS, AND BLOOD PRESSURE ANALYZING METHOD

CROSS-REFERENCE TO RELATED APPLICATION(S)

This application is a continuation of PCT application No. PCT/JP2016/075436, which was filed on Aug. 31, 2016 based on Japanese Patent Application (No. 2015-185316) filed on Sep. 18, 2015, the contents of which are incorporated herein by reference.

BACKGROUND

1. Technical Field

The present invention relates to a blood pressure analyzing apparatus, a blood pressure measuring apparatus, and a blood pressure analyzing method.

2. Background Art

Usually, a diurnal variation in blood pressure value of a living body is comparatively large. For the purpose of diagnosis etc., a sphygmomanometer may be therefore mounted on a subject to measure and record a blood pressure value of the subject periodically (e.g. at intervals of several hours). In this case, relevant information to a cause of a variation in the blood pressure value is measured together with the measurement of the blood pressure value and recorded in order to find out the cause of the variation in the blood pressure value accurately and easily (see JP-UM-A-62-157504 and JP-A-04-161143).

JP-UM-A-62-157504 discloses an apparatus which records a blood pressure value, exercise intensity and atmospheric temperature continuously to assist to find out a cause of a variation in the blood pressure value from the recorded information.

JP-A-04-161143 discloses an apparatus which records information of an acceleration sensor mounted on a living body and a blood pressure value, in association with each other, so that a correlation between an exercise amount and a variation in physiological function can be grasped in detail from the thus recorded information and useful for diagnosis.

A biological information measuring apparatus has been known as an apparatus suitable for measuring a blood pressure value continuously as in the apparatus described in JP-UM-A-62-157504 or JP-A-04-161143. The biological information measuring apparatus can measure biological information such as a pulse or a blood pressure value continuously (for every beat) using pressure pulse wave information which is detected by a pressure sensor in a state in which the pressure sensor is brought into direct contact with a living body part which an artery such as a radial artery of a wrist passes (see JP-A-2004-113368, JP-A-02-261421, JP-A-07-124130 and JP-A-01-242031).

In addition, JP-A-2003-199719 has described a blood pressure measuring apparatus which combines measurement of blood pressure based on an oscillometric method with measurement of photoelectric pulse waves to measure blood pressure for every beat. Based on a waveform of each of the photoelectric pulse waves, the blood pressure measuring apparatus can detect a case where a subject had large body motion or displaced a measurement height with respect to the heart of the subject so that the blood pressure measuring apparatus can correct the blood pressure value accordingly.

The apparatus described in JP-UM-A-62-157504 is assumed to measure the blood pressure value at long-time intervals of several minutes, several tens of minutes or several hours. When the blood pressure value is measured at such long-time intervals, it is however impossible for a doctor etc. to know a large blood pressure variation if the blood pressure variation occurred in a period in which the blood pressure value was not measured.

According to an apparatus measuring a blood pressure value for every beat as in the apparatus described in any of JP-A-2004-113368, JP-A-02-261421, JP-A-07-124130, JP-A-01-242031 and JP-A-2003-199719, the doctor etc. can grasp a small blood pressure variation caused by patient's daily life.

In a blood pressure measuring apparatus worn on a wrist of a subject, blood pressure varies due to the following two cases. That is, in the first case, a difference in height between a heart and the wrist of the subject varies. In the second case, abnormality (a cardiovascular event etc.) occurs in a body of the subject to result in sudden fluctuation in blood pressure. When the blood pressure measuring apparatus can distinguish those cases clearly, the blood pressure measuring apparatus is conceived to be largely useful for the doctor's diagnosis.

The apparatus described in any of JP-A-2004-113368, JP-A-02-261421, JP-A-07-124130 and JP-A-01-242031 is not assumed to determine a cause of a blood pressure variation. Therefore, the apparatus described in any of JP-A-2004-113368, JP-A-02-261421, JP-A-07-124130 and JP-A-01-242031 cannot distinguish the aforementioned two cases from each other.

The apparatus described in JP-A-04-161143 records a level of physical activity in daily life of a subject together with blood pressure information of the subject. However, the apparatus described in JP-A-04-161143 is not assumed to distinguish a case where a difference in height between a heart and a wrist of the subject varies to result in a variation in the blood pressure of the subject, from a case where abnormality occurs in the body of the subject to result in a variation in the blood pressure of the subject.

The apparatus described in JP-A-2003-199719 detects presence/absence of body motion or displacement of a measurement height with respect to a heart based on an output from the photoelectric pulse wave sensor. When a cardiovascular event occurs, the output of the photoelectric pulse wave sensor also fluctuates largely. For this reason, the apparatus described in JP-A-2003-199719 cannot distinguish a case where there was either large body motion or a displacement in the measurement height with respect to the heart, from a case where the cardiovascular event occurred.

SUMMARY

The invention has been accomplished in consideration of the aforementioned circumstances. An object of the invention is to provide a blood pressure analyzing apparatus, a blood pressure measuring apparatus, and a blood pressure analyzing method, which can determine a cause of a blood pressure variation useful for diagnosis.

According to an aspect of the invention, there is provided a blood pressure analyzing apparatus which analyzes a cause of a blood pressure variation of a subject from blood pressure values calculated every beat for a plurality of beats based on pulse waves detected from a wrist of the subject and wrist move information detected by a detector that detects a move of the wrist, the blood pressure values and the wrist move information that are recorded into a recording medium, the blood pressure analyzing apparatus comprising: a blood pressure variation determiner which determines whether a first blood pressure value varies a threshold or more from a second blood pressure value or not, the first blood pressure value corresponding to an arbitrary beat of the blood pressure values corresponding to the plurality of beats, the second blood pressure value corresponding to a previous beat to the arbitrary beat of the blood pressure values corresponding to the plurality of beats; a blood pressure variation cause determiner which determines whether the blood pressure variation is caused by the move of the wrist or by another reason than the move of the wrist, based on, of the wrist move information recorded into the recording medium, wrist move information detected in a detection period of a pulse wave serving as a calculation source of the first blood pressure value, when it is determined that the first blood pressure value varies the threshold or more from the second blood pressure value; and a recording controller which records, into a recording medium, a determination result made by the blood pressure variation cause determiner and the first blood pressure value in association with each other.

According to an aspect of the invention, there is also provided a blood pressure analyzing method which analyzes a cause of a blood pressure variation of a subject from blood pressure values calculated every beat for a plurality of beats based on pulse waves detected from a wrist of the subject and wrist move information detected by a detector that detects a move of the wrist, the blood pressure values and the wrist move information that are recorded into a recording medium, the blood pressure analyzing method comprising: acquiring the blood pressure values corresponding to the plurality of beats recorded into the recording medium and the wrist move information detected during a detection period of the pulse waves serving as a calculation source of the blood pressure values corresponding to the plurality of beats; determining whether a first blood pressure value varies a threshold or more from a second blood pressure value or not, the first blood pressure value corresponding to an arbitrary beat of the acquired blood pressure values corresponding to the plurality of beats, the second blood pressure value corresponding to a previous beat to the arbitrary beat of the blood pressure values corresponding to the plurality of beats; determining whether the blood pressure variation is caused by the move of the wrist or by another reason than the move of the wrist, based on, of the acquired wrist move information, wrist move information detected in a detection period of a pulse wave serving as a calculation source of the first blood pressure value, when it is determined that the first blood pressure value varies the threshold or more from the second blood pressure value; and recording, into a recording medium, a determination result of whether the blood pressure variation is caused by the move of the wrist or by another reason than the move of the wrist and the first blood pressure value in association with each other.

DESCRIPTION OF EXEMPLARY EMBODIMENTS

An embodiment of the invention will be described below with reference to the drawings.

Figure 1:
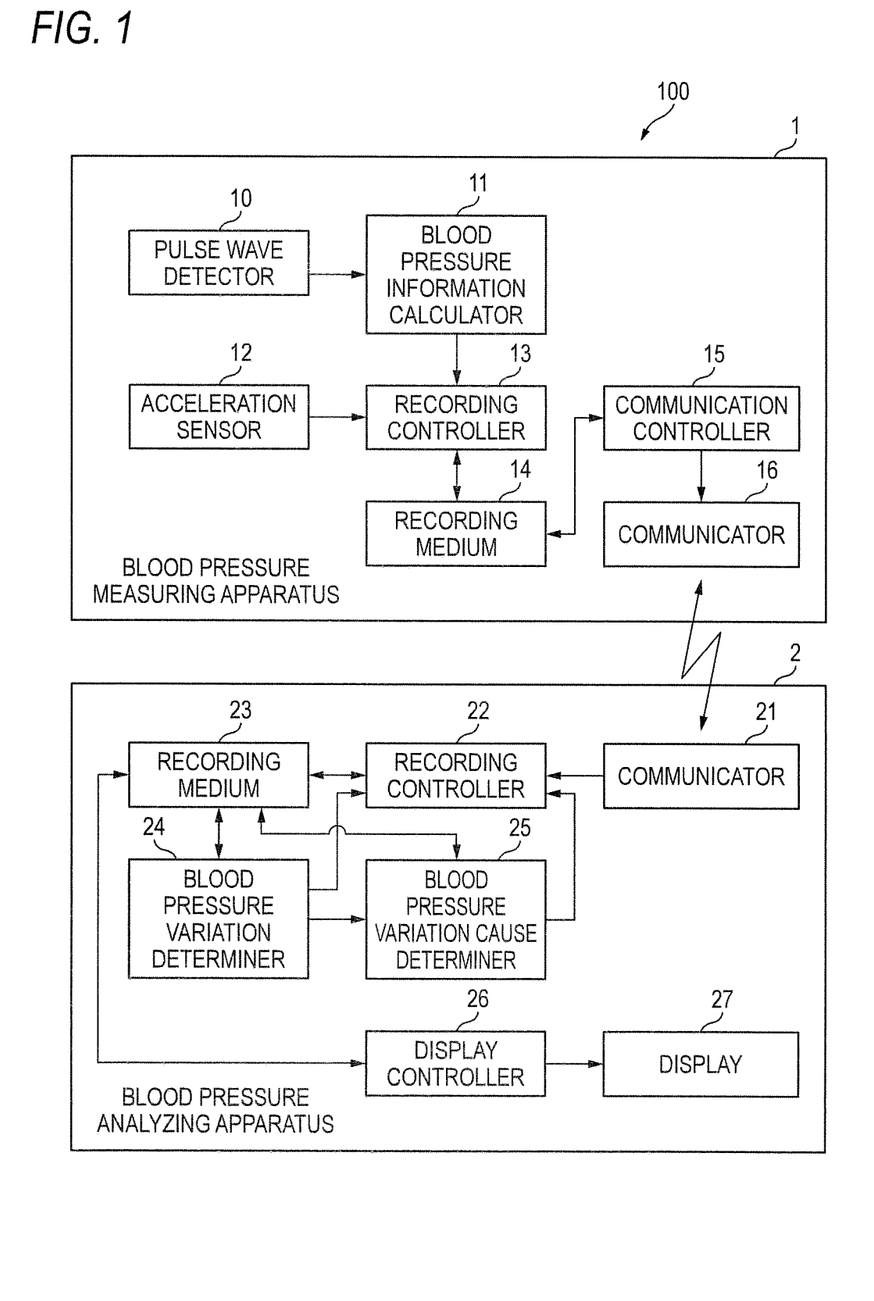
FIG. 1 is a diagram schematically showing the configuration of a blood pressure management system 100 for explaining an embodiment of the invention.

FIG. 1 is a diagram schematically showing the configuration of a blood pressure management system 100 for explaining the embodiment of the invention. The blood pressure management system 100 includes a blood pressure measuring apparatus 1 and a blood pressure analyzing apparatus 2.

The blood pressure measuring apparatus 1 is a portable type which is used to be worn on a wrist of a subject regarded as a living body.

The blood pressure measuring apparatus 1 includes a pulse wave detector 10, a blood pressure information calculator 11, an acceleration sensor 12, a recording controller 13, a recording medium 14 such as a flash memory, an ROM (Read Only Memory) or a memory card, a communication controller 15, and a communicator 16. The recording medium 14 may be attachable to or detachable from the apparatus.

The blood pressure information calculator 11, the recording controller 13 and the communication controller 15 are functional blocks which are realized by a processor executing a program.

The pulse wave detector 10 detects pulse waves in a noninvasive manner from the wrist of the subject. The pulse wave detector 10 is used for detecting pressure pulses wave as the pulse waves, for example, by a tonometry method. The pulse wave detector 10 may detect volume pulse waves as the pulse waves. The pulse wave detector 10 may detect the pulse waves by reflected light obtained from an artery irradiated with light.

The pulse wave detector 10 detects the pulse waves occurring for every beat (in every period in which the heart beats once) to transmit the detected pulse waves to the blood pressure information calculator 11.

The blood pressure information calculator 11 calculates blood pressure information for every beat based on the pulse waves detected by the pulse wave detector 10. To calculate blood pressure information for every beat means to calculate blood pressure information every beat or to calculate blood pressure information every multiple beats (e.g. every two beats).

The blood pressure information may include systolic blood pressure SBP, diastolic blood pressure DBP, and mean blood pressure MBP.

Any of known methods as described in JP-A-2004-113368, JP-A-02-261421, JP-A-07-124130 and JP-A-01-242031 can be used as a blood pressure information calculating method. The blood pressure information calculator 11 transmits, to the recording controller 13, detection period information and blood pressure information in association with each other. The detection period information indicates a time for a detection period of an arbitrary pulse wave. The blood pressure information is calculated based on the pulse wave.

The acceleration sensor 12 is a detector which detects a move of the wrist of the subject directly. In the embodiment, a triaxial acceleration sensor is used as the acceleration sensor 12. Triaxial acceleration information detected by the acceleration sensor 12 is transmitted to the recording controller 13. An angular velocity sensor or an atmospheric pressure sensor may be used as the detector.

The recording controller 13 records, into the recording medium 14, a set of the pulse wave detection period information and the blood pressure information transmitted from the blood pressure information calculator 11.

In addition, the recording controller 13 records, into the recording medium 14, the acceleration information transmitted from the acceleration sensor 12, in association with a detection time of the acceleration information.

By control of the recording controller 13, blood pressure information corresponding to a plurality of beats calculated by the blood pressure information calculator 11, and wrist move information (triaxial acceleration information) detected by the acceleration sensor 12 during a pulse wave detection period serving as a calculation source of the blood pressure information corresponding to the plurality of beats are recorded into the recording medium 14.

The communicator 16 is an interface for performing communication with an external device by wire or by wireless.

The communication controller 15 performs control to transmit transmission data to the external device through the communicator 16. The transmission data include the blood pressure information corresponding the plurality of beats which have been recorded into the recording medium 14, and the acceleration information which have been detected by the acceleration sensor 12 during the pulse wave detection period serving as the calculation source of the blood pressure information corresponding to the plurality of beats.

The blood pressure analyzing apparatus 2 includes a communicator 21, a recording controller 22, a recording medium such as a flash memory, an ROM or a memory card, a blood pressure variation determiner 24, a blood pressure variation cause determiner 25, a display controller 26, and a display 27. The recording medium 23 may be attachable to or detachable from the apparatus.

The recording controller 22, the blood pressure variation determiner 24 and the blood pressure variation cause determiner 25 are functional blocks which are realized by a processor executing a program.

The blood pressure analyzing apparatus 2 may be a dedicated apparatus for analysis of blood pressure or may be a general-purpose electronic device such as a smartphone or a tablet terminal.

The communicator 21 is an interface for performing communication with an external device by wire or by wireless.

The recording controller 22 performs control to acquire the aforementioned transmission data which have been received from the blood pressure measuring apparatus 1 by the communicator 21, and to record the acquired transmission data into the recording medium 23.

The blood pressure variation determiner 24 determines whether, of the blood pressure information corresponding to the plurality of beats, first blood pressure information corresponding to an arbitrary beat varies a threshold TH1 or more from, of the blood pressure information corresponding to the plurality of beats, second blood pressure information corresponding to a previous beat to the arbitrary beat (blood pressure information corresponding to a beat immediate before the arbitrary beat or an average value of blood pressure information corresponding to a plurality of consecutive beats before the arbitrary beat) or not. The blood pressure information corresponding to the plurality of beats are included in the transmission data which have been acquired from the blood pressure measuring apparatus 1 and recorded into the recording medium 23. The blood pressure information corresponding to the arbitrary beat means a blood pressure information calculated based on a pulse wave detected at the arbitrary beat.

When the first blood pressure information varies the threshold TH1 or more from the second blood pressure information, the blood pressure variation determiner 24 transmits, to the blood pressure variation cause determiner 25, information indicating presence of a blood pressure variation and a difference value (blood pressure variation amount) between the first blood pressure information and the second blood pressure information in association with the first blood pressure information.

When the first blood pressure information does not vary the threshold TH1 or more from the second blood pressure information, the blood pressure variation determiner 24 transmits, to the recording controller 22, information indicating absence of a blood pressure variation in association with the first blood pressure information.

About the blood pressure information which has been transmitted from the blood pressure variation determiner 24, the blood pressure variation cause determiner 25 determines whether the blood pressure variation is caused by a move of the wrist or by another reason than the move of the wrist, based on, of the wrist move information which have been recorded into the recording medium 23, wrist move information detected during a pulse wave detection period serving as a calculation source of the blood pressure information.

The blood pressure variation cause determiner 25 transmits, to the recording controller 22, the blood pressure information with which the information indicating the presence of the blood pressure variation and the blood pressure variation amount have been associated, and a determination result of the cause of the blood pressure variation regarding the blood pressure information.

Table data in which a variation amount of a height of a wrist with respect to a reference position, and a variation amount of blood pressure information detected from a pulse wave are associated with each other is recorded in advance in the recording medium 23.

Figure 2:
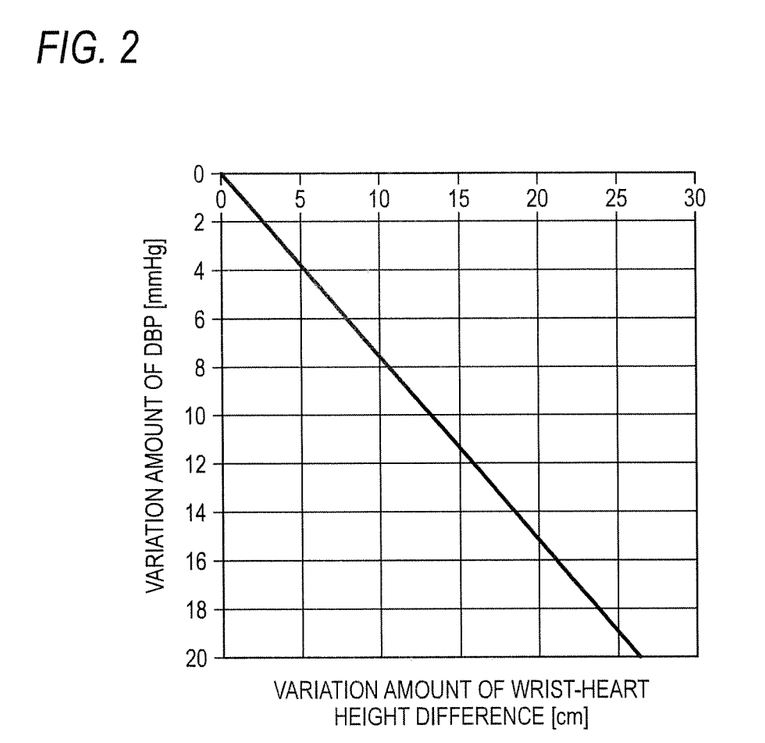
FIG. 2 is a chart explaining processing contents of a blood pressure variation determiner 24 and a blood pressure variation cause determiner 25 of a blood pressure analyzing apparatus 2 in FIG. 1.

FIG. 2 is a chart showing an example of the table data recorded into the recording medium 23. As shown in FIG. 2, the table data are data showing how much the blood pressure information varies in accordance with how much the height of the wrist varies with respect to the reference position. Specifically, the reference position is a position of a heart.

A subject wearing the blood pressure measuring apparatus 1 is instructed to assume a posture so as to make his/her wrist in line with a position of his/her heart. Then, the subject is requested to put his/her wrist up/down from this posture. In this manner, the table data can be generated using blood pressure information calculated in a period in which the subject is putting his/her wrist up/down.

For example, from the table data of FIG. 2, it can be known that when the difference in height between the wrist and the reference position (heart) varies 8 cm, DBP varies 6 mmHg.

The table data recorded into the recording medium 23 may be generated from a relationship between the difference in height between the wrist and the heart and water head pressure. When the table data are generated using first-hand blood pressure information measured from the subject, accuracy of the table data can be increased.

About the blood pressure information which has been transmitted from the blood pressure variation determiner 24, the recording controller 22 records, into the recording medium 23, the information indicating the absence of the blood pressure variation, in association with the blood pressure information.

Of the blood pressure information which have been transmitted from the blood pressure variation cause determiner 25, as to blood pressure information in which a blood pressure variation is caused by a move of the wrist, the recording controller 22 uses the table data of FIG. 2 to obtain a variation amount of the height of the wrist with respect to the reference position correspondingly to the blood pressure variation amount associated with the blood pressure information.

The recording controller 22 records, into the recording medium 23, information indicating presence of the blood pressure variation, information indicating that the blood pressure variation is caused by the move of the wrist, and the variation amount of the difference in height between the wrist and the heart, in association with the blood pressure information.

Of the blood pressure information which have been transmitted from the blood pressure variation cause determiner 25, as to blood pressure information in which a blood pressure variation is caused by another reason than the move of the wrist, the recording controller 22 records, into the recording medium 23, information indicating presence of the blood pressure variation, information indicating that the blood pressure variation is caused by another reason than the move of the wrist, and the blood pressure variation amount, in association with the blood pressure information.

Figure 3:
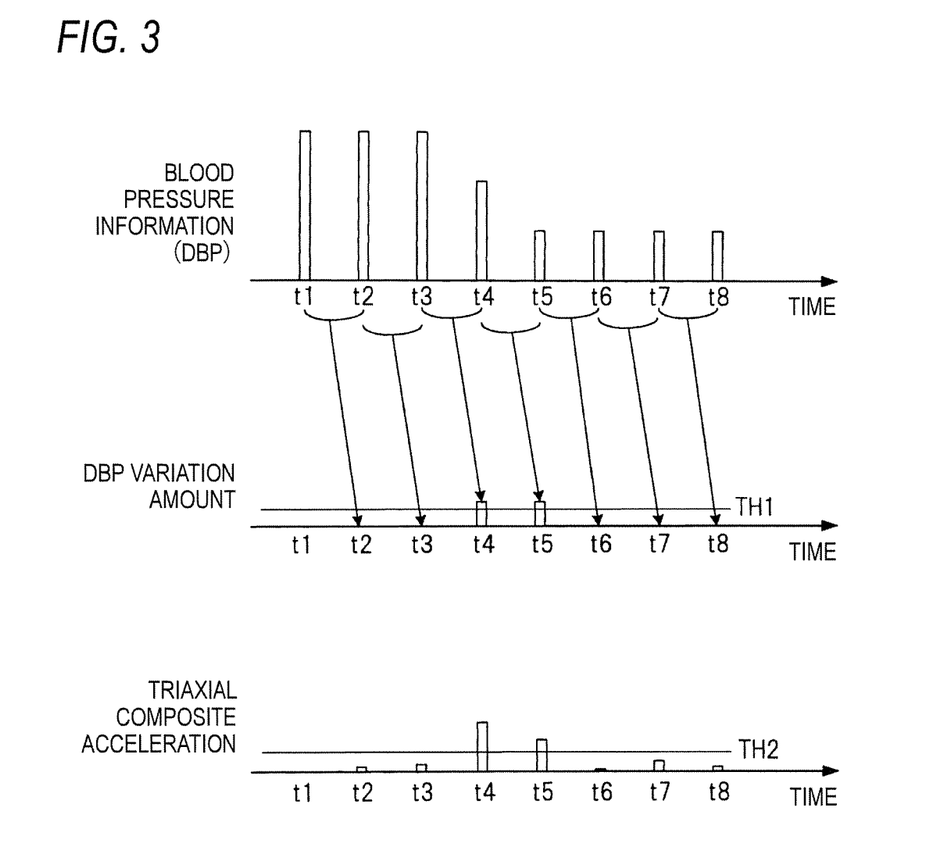
FIG. 3 is a view showing an example of table data which are stored in the blood pressure analyzing apparatus 2 in FIG. 1 and express a relationship between a variation amount in blood pressure and a variation amount in wrist-heart height difference.

FIG. 3 is a view for specifically explaining processing contents of the blood pressure variation determiner 24 and the blood pressure variation cause determiner 25. Each blood pressure information will be hereinafter described as DBP.

DBPs corresponding to a plurality of beats, which have been recorded into the recording medium 23, are shown in an upper part of FIG. 3. Each white blank rectangle shown in FIG. 3 designates a DBP, representing that the longer the rectangle is, the larger the DBP is. Times t1 to t8 are pulse wave detection times which are calculation sources of the respective DBPs.

The blood pressure variation determiner 24 arithmetically processes a difference between a DBP corresponding to a time $t_n$ (n=1 to 8) and a DBP corresponding to a time $t_{n-1}$ previous to a time $t_n$. When the difference is a threshold TH1 or more, the blood pressure variation determiner 24 determines that a blood pressure variation is present at the time $t_n$. When the difference is smaller than the threshold TH1, the blood pressure variation determiner 24 determines that a blood pressure variation is absent at the time $t_n$.

Incidentally, instead of arithmetically processing the difference between the DBP corresponding to the time $t_n$ and the DBP corresponding to the time $t_{n-1}$, a difference between the DBP corresponding to the time $t_n$ and an average value of DBPs corresponding to a plurality of consecutive times previous to the time $t_n$ may be arithmetically processed.

Results obtained by taking differences between adjacent ones of the DBPs in the uppermost part of FIG. 3 are shown in a middle part of FIG. 3. In FIG. 3, a difference value between the DBP corresponding to the time $t_n$ and the DBP corresponding to the time $t_{n-1}$ is illustrated as a difference value corresponding to the time $t_n$.

In the example of FIG. 3, each of a difference value corresponding to the time t4 and a difference value corresponding to the time t5 exceeds the threshold TH1. Therefore, it is determined that a blood pressure variation is present at each of the time t4 and the time t5.

Composite acceleration of triaxial accelerations detected by the acceleration sensor 12 at each of the times t1 to t8 is shown in a lower part of FIG. 3. The longer each white blank rectangle in the lower part of FIG. 3 is, the larger the composite acceleration is.

As to the DBP corresponding to the time $t_n$ at which it is determined that the blood pressure variation is present, the blood pressure variation cause determiner 25 determines whether or not the composite acceleration of the triaxial accelerations detected during a pulse wave detection period serving as a calculation source of the DBP is equal to or larger than a threshold TH2.

When the composite acceleration is equal to or larger than the threshold TH2, the blood pressure variation cause determiner 25 determines that the blood pressure variation is caused by a move of the wrist. When the composite acceleration is smaller than the threshold TH2, the blood pressure variation cause determiner 25 determines that the blood pressure variation is caused by another reason than the move of the wrist.

In the example of FIG. 3, it is determined that the blood pressure variation at each of the time t4 and the time t5 is caused by the move of the wrist.

Return to the explanation of FIG. 1. The display 27 serves for displaying data etc. recorded in the recording medium 23. The display 27 is constituted by a liquid crystal display device or the like.

The display controller 26 controls the display 27.

When the blood pressure measuring apparatus 1 configured in the aforementioned manner is worn on the subject and powered on, detection of each pulse wave is started by the pulse wave detector 10, and detection of acceleration information is started by the acceleration sensor 12.

When the pulse wave is detected, blood pressure information is calculated by the blood pressure information calculator 11, and the blood pressure information, detection period information of the pulse wave used for the calculation of the blood pressure information, and the acceleration information are recorded into the recording medium 14.

After the subject has used the blood pressure measuring apparatus 1 for a fixed period (e.g. one day), the subject goes to a hospital and operates a not-shown operating button to thereby transmit transmission data including the blood pressure information, the detection period information and the acceleration information to the blood pressure analyzing apparatus 2 placed in the hospital. The blood pressure information, the detection period information and the acceleration information have been recorded into the recording medium 14.

Figure 4:
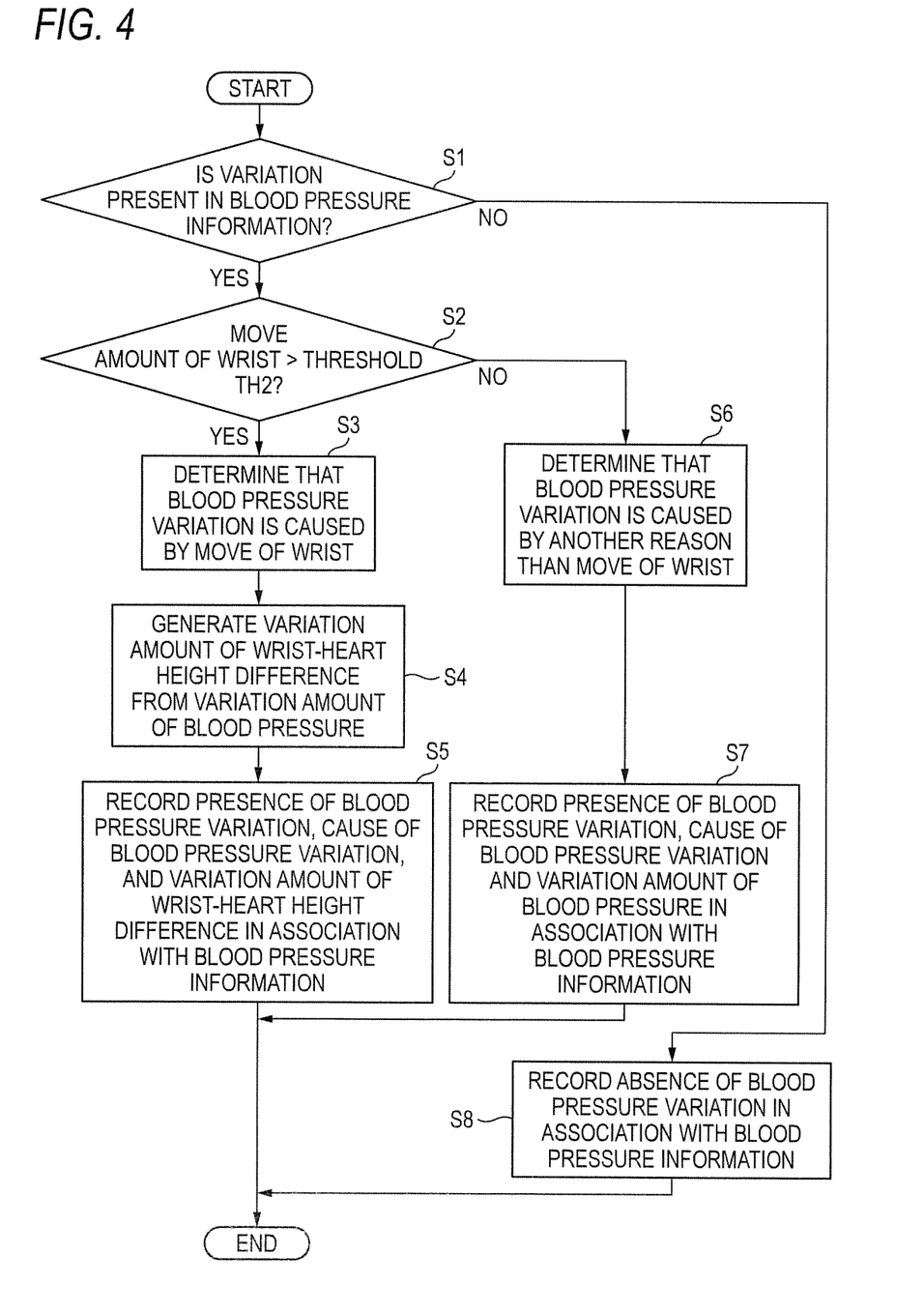
FIG. 4 is a flow chart for explaining operation of the blood pressure analyzing apparatus 2 in FIG. 1.

FIG. 4 is a flow chart for explaining operation of the blood pressure analyzing apparatus 2 after the transmission data have been received.

The recording controller 22 of the blood pressure analyzing apparatus 2 acquires the transmission data received by the communicator 21, and records the acquired transmission data into the recording medium 23.

The blood pressure variation determiner 24 targets, of blood pressure information corresponding to a plurality of beats included in the transmission data recorded into the recording medium 23, first blood pressure information corresponding to an arbitrary beat, calculates a difference value (blood pressure variation amount) between the first blood pressure information and second blood pressure information which has been calculated one beat before the first blood pressure information, and determines whether or not the calculated difference value is equal to or larger than a threshold TH1 (whether a variation is present or absent in the blood pressure information) (step S1).

When the determination of the step S1 is NO, the recording controller 22 records, into the recording medium 23, information indicating that the blood pressure variation is absent, in association with the first blood pressure information (step S8).

When the determination of the step S1 is YES, the blood pressure variation cause determiner 25 determines whether or not composite acceleration of triaxial acceleration information (a move amount of the wrist) during a pulse wave detection period serving as a calculation source of the first blood pressure information is equal to or larger than a threshold TH2 (step S2).

When the determination of the step S2 is YES, the blood pressure variation cause determiner 25 determines that the blood pressure variation is caused by the move of the wrist (step S3).

After the step S3, from the blood pressure variation amount calculated in the step S1 and table data recorded into the recording medium 23, the recording controller 22 obtains a variation amount of a height of the wrist with respect to a reference position correspondingly to the blood pressure variation amount (step S4).

After the step S4, the recording controller 22 records, into the recording medium 23, the variation amount obtained in the step S4, information indicating that the blood pressure variation is present, and information indicating that the blood pressure variation is caused by the move of the wrist, in association with the first blood pressure information (step S5).

When the determination of the step S2 is NO, the blood pressure variation cause determiner 25 determines that the blood pressure variation is caused by another reason than the move of the wrist (step S6).

After the step S6, the recording controller 22 records, into the recording medium 23, information indicating that the blood pressure variation is present, information indicating that the blood pressure variation is caused by another reason than the move of the wrist, and the blood pressure variation amount calculated in the step S1, in association with the first blood pressure information (step S7).

The aforementioned processing is carried out on blood pressure information corresponding to all beats which have been recorded into the recording medium 23. Each of the blood pressure information recorded into the recording medium 23 by the processing performed thus and information associated with the blood pressure information are displayed on the display 27 by control of the display controller 26.

Thus, a doctor using the blood pressure analyzing apparatus 2 can easily grasp a change in the blood pressure information of the subject for every beat or every multiple beats, and a cause of a blood pressure variation when a large variation occurs in the blood pressure information.

The doctor can instantaneously grasp whether or not there is any blood pressure information with which information indicating that the blood pressure variation is caused by another reason than the move of the wrist has been associated. Therefore, the doctor can easily judge a risk of a cardiovascular event (a stroke, myocardial infarction, or the like) of the subject.

According to the blood pressure management system 100 in FIG. 1, as described above, it is possible to assist to accurately grasp the cause of the variation in the blood pressure information of the subject.

Alternatively, the blood pressure measuring apparatus 1 may have the functions of the recording controller 22, the blood pressure variation determiner 24, and the blood pressure variation cause determiner 25 of the blood pressure analyzing apparatus 2. In this case, for example, the subject may issue an instruction to analyze data at the end of one day. When the instruction is issued, the processing described in FIG. 4 is started, and various information are associated with each blood pressure information which has been calculated on that day and recorded into the recording medium 14.

With this configuration, the blood pressure information and the information associated with the blood pressure information may be acquired from the recording medium 14 of the blood pressure measuring apparatus 1 by a computer etc. placed in a medical institution so that a doctor can check these information. Thus, introduction cost of the system in the medical institution can be reduced.

The functions of the recording controller 22, the blood pressure variation determiner 24, and the blood pressure variation cause determiner 25 of the blood pressure analyzing apparatus 2 are designed to be realized by a processor executing a program. It is preferable that the program can be downloaded through a network such as the Internet.

With this configuration, a tablet terminal, a smartphone or a personal computer existing in the medical institution can be used as the blood pressure analyzing apparatus 2 easily. Therefore, the medical institution can suppress the introduction cost of the system.

Such a program may be recorded into a non-transitory computer-readable recording medium and provided to the medical institution etc. Examples of such a "computer-readable recording medium" include an optical medium such as a CD-ROM (Compact Disc-ROM), a magnetic recording medium such as a memory card, etc.

DBP, SBP and MBP can be used as the blood pressure information by the blood pressure variation determiner 24 in order to determine presence/absence of a blood pressure variation. Of them, it is known that the SBP fluctuates largely even in a normal state. Therefore, it is preferable that the DBP or the MBP is used as the blood pressure information in order to determine presence/absence of a blood pressure variation.

Any device may be used as the acceleration sensor 12 of the blood pressure measuring apparatus 1 as long as the device can detect a move of a wrist. For example, a combination of an acceleration sensor and an angular velocity sensor may be used.

When one blood pressure information is calculated every multiple beats (e.g. once every two beats), the blood pressure information calculator 11 of the blood pressure measuring apparatus 1 can reduce a volume of data to be recorded into the recording medium 14. Therefore, manufacturing cost of the blood pressure measuring apparatus 1 can be reduced due to the reduction in the capacity of the recording medium 14.

In the case where some blood pressure information are recorded while the other blood pressure information are thinned out, it may become difficult to grasp a cause of a blood pressure variation of a subject if the number of the blood pressure information which have been thinned out is too large. Therefore, it is preferable that thinning is suppressed to such an extent that one blood pressure information is recorded into the recording medium 14 every two to ten beats.

It should be conceived that all the points in the embodiment disclosed this time are not limited but merely exemplified. The scope of the invention is defined not by the aforementioned description but by the scope of Claims. All changes having equivalent meaning to the scope of Claims and within the scope of Claims are intended to be included in the scope of the invention.

As described above, the following matters are disclosed in the description of the invention.

Provided is the disclosed blood pressure analyzing apparatus including: a blood pressure variation determiner which determines whether first blood pressure information varies a threshold or more from second blood pressure information or not, the first blood pressure information corresponding to an arbitrary beat of blood pressure information, the second blood pressure information corresponding to a previous beat to the arbitrary beat of the blood pressure information, the blood pressure information corresponding to a plurality of beats which are calculated for every beat based on pulse waves detected from a wrist of a subject and which are recorded into a recording medium, the recording medium that records the blood pressure information corresponding to the plurality of beats and wrist move information detected by a detector, the detector that detects a move of the wrist during a detection period of the pulse waves serving as a calculation source of the blood pressure information corresponding to the plurality of beats; a blood pressure variation cause determiner which determines whether a blood pressure variation is caused by the move of the wrist or by another reason than the move of the wrist, based on, of the wrist move information recorded into the recording medium, wrist move information detected in a detection period of a pulse wave serving as a calculation source of the first blood pressure information, when it is determined that the first blood pressure information varies the threshold or more from the second blood pressure information; and a recording controller which records a determination result made by the blood pressure variation cause determiner and the first blood pressure information in association with each other.

Provided is the disclosed blood pressure analyzing apparatus further including: a recorder which records data in which a variation amount of blood pressure information and a variation amount of a height of the wrist with respect to a reference position are associated with each other, wherein the recording controller further records a variation amount of the height of the wrist corresponding to a difference between the first blood pressure information and the second blood pressure information, in association with the first blood pressure information with which information indicating that the blood pressure variation is caused by the move of the wrist is associated.

In the disclosed blood pressure analyzing apparatus, each of the first blood pressure information and the second blood pressure information is diastolic blood pressure or mean blood pressure.

Provided is the disclosed blood pressure measuring apparatus including: a blood pressure information calculator which calculates blood pressure information every beat for a plurality of beats based on pulse waves detected from a wrist of the subject; a detector which detects a move of the wrist; and a recording controller which records, into the recording medium, the blood pressure information corresponding to the plurality of beats calculated by the blood pressure information calculator, and wrist move information detected by the detector during a detection period of the pulse waves serving as a calculation source of the blood pressure information corresponding to the plurality of beats.

Provided is the disclosed blood pressure analyzing method including: an acquisition step of acquiring blood pressure information corresponding to a plurality of beats calculated for every beat based on pulse waves detected from a wrist of a subject and wrist move information detected by a detector that detects a move of the wrist during a detection period of the pulse waves serving as a calculation source of the blood pressure information corresponding to the plurality of beats, from a recording medium that records the blood pressure information corresponding to the plurality of beats and the wrist move information; a blood pressure variation determination step of determining whether first blood pressure information varies a threshold or more from second blood pressure information or not, the first blood pressure information corresponding to an arbitrary beat of the acquired blood pressure information corresponding to the plurality of beats, the second blood pressure information corresponding to a previous beat to the arbitrary beat of the blood pressure information corresponding to the plurality of beats; a blood pressure variation cause determination step of determining whether a blood pressure variation is caused by the move of the wrist or by another reason than the move of the wrist, based on, of the acquired wrist move information, wrist move information detected in a detection period of a pulse wave serving as a calculation source of the first blood pressure information, when it is determined that the first blood pressure information varies the threshold or more from the second blood pressure information; and a recording control step of recording a determination result made by the blood pressure variation cause determination step and the first blood pressure information in association with each other.

Provided is the disclosed blood pressure analyzing program which causes a computer to execute respective steps of the blood pressure analyzing method.

According to the invention, it is possible to provide a blood pressure analyzing apparatus, a blood pressure measuring apparatus, a blood pressure analyzing method and a blood pressure analyzing program, which can accurately determine a cause of a blood pressure variation useful for diagnosis.

The invention can accurately determine a cause of a blood pressure variation useful for diagnosis. Accordingly, the invention can be used in a medical institution.

Although the invention has been described based on a specific embodiment, the invention is not limited to the embodiment. Various changes can be however made on the invention without departing from the technical concept of the disclosed invention.

What is claimed is:

1. A blood pressure analyzing apparatus which analyzes a cause of a blood pressure variation of a subject from blood pressure values calculated every beat for a plurality of beats based on pulse waves detected from a wrist of the subject and wrist move information detected by a detector that detects a move of the wrist, the blood pressure values and the wrist move information that are recorded into a recording medium, the blood pressure analyzing apparatus comprising:

a processor which
determines whether a first blood pressure value varies a first threshold or more from a second blood pressure value or not, the first blood pressure value corresponding to an arbitrary beat of the blood pressure values corresponding to the plurality of beats, the second blood pressure value corresponding to a previous beat to the arbitrary beat of the blood pressure values corresponding to the plurality of beats;

determines whether the blood pressure variation is caused by the move of the wrist or by another reason than the move of the wrist, based on, of the wrist move information recorded into the recording medium, whether the wrist move information detected in a detection period of a pulse wave serving as a calculation source of the first blood pressure value, when it is determined that the first blood pressure value varies the first threshold or more from the second blood pressure value; and records, into a recording medium, a determination result of a blood pressure variation cause made by the processor and the first blood pressure value in association with each other, wherein the blood pressure variation is determined to be caused by the move of the wrist when the wrist move information detected in the detection period is a second threshold or greater, wherein the processor records data in which a variation amount of a blood pressure value and a variation amount of a height of the wrist with respect to a reference position are associated with each other, wherein the processor obtains the variation amount of the height of the wrist corresponding to a blood pressure variation amount, which is a difference between the first blood pressure value and the second blood pressure value, from the blood pressure variation amount and the data, and wherein the processor further records the variation amount of the height of the wrist corresponding to the blood pressure variation amount, in association with the first blood pressure value with which information indicating that the blood pressure variation is caused by the move of the wrist is associated.

2. The blood pressure analyzing apparatus according to claim 1, wherein each of the first blood pressure value and the second blood pressure value is diastolic blood pressure or mean blood pressure.

3. A blood pressure measuring apparatus comprising:

the blood pressure analyzing apparatus according to claim 1;

a blood pressure information calculator which calculates blood pressure values every beat for a plurality of beats based on pulse waves detected from a wrist of the subject; and a detector which detects a move of the wrist, wherein the processor further records, into the recording medium, the blood pressure values corresponding to the plurality of beats calculated by the blood pressure information calculator, and wrist move information detected by the detector during a detection period of the pulse waves serving as a calculation source of the blood pressure values corresponding to the plurality of beats.

4. A blood pressure analyzing method which analyzes a cause of a blood pressure variation of a subject from blood pressure values calculated every beat for a plurality of beats based on pulse waves detected from a wrist of the subject and wrist move information detected by a detector that detects a move of the wrist, the blood pressure values and the wrist move information that are recorded into a recording medium, the blood pressure analyzing method comprising:

acquiring the blood pressure values corresponding to the plurality of beats recorded into the recording medium and the wrist move information detected during a detection period of the pulse waves serving as a calculation source of the blood pressure values corresponding to the plurality of beats by a processor;

determining whether a first blood pressure value varies a first threshold or more from a second blood pressure value or not, the first blood pressure value corresponding to an arbitrary beat of the acquired blood pressure values corresponding to the plurality of beats, the second blood pressure value corresponding to a previous beat to the arbitrary beat of the blood pressure values corresponding to the plurality of beats by the processor;

determining whether the blood pressure variation is caused by the move of the wrist or by another reason than the move of the wrist, based on, of the acquired wrist move information, wrist move information detected in a detection period of a pulse wave serving as a calculation source of the first blood pressure value, when it is determined that the first blood pressure value varies the first threshold or more from the second blood pressure value by the processor;

recording, into a recording medium, a determination result of whether the blood pressure variation is caused by the move of the wrist or by another reason than the move of the wrist and the first blood pressure value in association with each other by the processor;

recording data in which a variation amount of a blood pressure value and a variation amount of a height of the wrist with respect to a reference position are associated with each other by the processor, obtaining the variation amount of the height of the wrist corresponding to a blood pressure variation amount, which is a difference between the first blood pressure value and the second blood pressure value, from the blood pressure variation amount and the data, by the processor, and further recording the variation amount of the height of the wrist corresponding to the blood pressure variation amount, in association with the first blood pressure value with which information indicating that the blood pressure variation is caused by the move of the wrist is associated, by the processor, wherein the blood pressure variation is determined to be caused by the move of the wrist when the wrist move information detected in the detection period is a second threshold or greater.

5. A non-transitory computer-readable recording medium in which a program causing a computer to execute the blood pressure analyzing method according to claim 4 is recorded.

* * * * *